United States Patent [19]

Ingebrethsen

[11] Patent Number: 5,388,574
[45] Date of Patent: Feb. 14, 1995

[54] AEROSOL DELIVERY ARTICLE

[76] Inventor: Bradley J. Ingebrethsen, 3522 Kittery Ct., Winston-Salem, N.C. 27104

[21] Appl. No.: 99,015

[22] Filed: Jul. 29, 1993

[51] Int. Cl.$^6$ .......................................... A61M 15/00
[52] U.S. Cl. ........................... 125/203.17; 125/200.16; 125/203.26
[58] Field of Search ....................... 128/200.14, 200.15, 128/200.16, 200.17, 200.18, 200.19, 200.20, 200.21, 200.22, 200.23, 203.16, 203.17, 203.26

[56] References Cited

U.S. PATENT DOCUMENTS

| | | | |
|---|---|---|---|
| 1,771,366 | 7/1930 | Wyss et al. | |
| 1,968,509 | 7/1934 | Tiffany | 219/38 |
| 2,030,075 | 2/1936 | Robinson | 128/92 |
| 2,057,353 | 10/1936 | Whittemore, Jr. | 219/38 |
| 2,248,591 | 5/1942 | Rose | 299/38 |
| 2,332,799 | 10/1943 | Hunn et al. | 128/175 |
| 2,764,154 | 9/1956 | Murai | 128/201 |
| 3,297,029 | 1/1967 | Brinkman et al. | 128/188 |
| 3,820,540 | 6/1974 | Hirtz et al. | 128/212 |
| 3,859,398 | 1/1975 | Havstad | 261/141 |
| 3,864,544 | 2/1975 | van Amerongen | 219/301 |
| 3,990,441 | 11/1976 | Hoyt et al. | 128/193 |
| 4,036,224 | 7/1977 | Choporis et al. | 128/212 |
| 4,190,046 | 2/1980 | Virag | 128/200 |
| 4,214,146 | 7/1980 | Schimanski | 219/274 |
| 4,303,083 | 12/1981 | Burruss, Jr. | 131/271 |
| 4,523,589 | 6/1985 | Krauser | 128/203 |
| 4,655,229 | 4/1987 | Sensabaugh, Jr. et al. | 131/273 |
| 4,655,959 | 4/1987 | Stopper | 252/305 |
| 4,715,387 | 12/1987 | Rose | 131/270 |
| 4,735,217 | 4/1988 | Gerth et al. | 131/273 |
| 4,765,347 | 8/1988 | Sensabaugh, Jr. et al. | 131/270 |
| 4,832,012 | 5/1989 | Raabe et al. | 128/200.21 |
| 4,922,901 | 5/1990 | Brooks et al. | 128/203 |
| 4,941,482 | 7/1990 | Ridings et al. | 131/194 |
| 4,951,659 | 8/1990 | Weiler et al. | 128/200.18 |
| 4,963,367 | 10/1990 | Ecanow | 424/485 |
| 5,145,604 | 9/1992 | Neumiller | 252/312 |

OTHER PUBLICATIONS

Paul C. Hiemenz; Principles of Colloid and Surface Chemistry; 1986; pp. 467–474.
Anthony J. Hickey; Summary of Common Approaches to Pharmaceutical Aerosol Administration; (1992); 255–288.
Giuseppe Tarroni, et al; An Indication on the Biological Variability of Aerosol Total Deposition in Humans; Am. Ind. Hyg. Assoc. J.; 41; Nov. 1980; pp. 826–831.
Richard N. Berglung, et al; Generation of Monodisperse Aerosol Standards; Environ Sci Technol vol. 7, No. 2, Feb., 1973; pp. 147–153.
M. J. Fulwyler; Electronic Separation of Biological Cells by Volume; Science, vol. 150; 1965; pp. 910–911.
Lars Strom; The Generation of Monodisperse Aerosols by Means of a Disintergrated Jet of Liquid; The Review of Scientific Instruments; vol. 40, No. 6; Jun., 1969; pp. 778–782.
Vittorio Prodi, A Condensation Aerosol Generator for Solid Monodisperse Particles; Assessment of Airborne Particles Fundamentals Applications and Implications to Inhalation Toxicity; 1972; pp. 169–181.
C. N. Davies; Generation and use of Monodisperse Aerosols; Aerosol Science; 1966; pp. 1–30.

*Primary Examiner*—Edgar S. Burr
*Assistant Examiner*—Eric Raciti

[57] ABSTRACT

An aerosol delivery article provides delivery of aerosol particles of relatively small size without the necessity of exposing the material which is aerosolized to a significant degree of heat or high temperatures. An aerosol forming material is a multi-component material comprising an active ingredient and another ingredient having a relatively low vaporization temperature, and preferably that aerosol forming material is in the form of an emulsion. The aerosol forming material is nebulized so as to provide first stage multi-component aerosol particles of fairly large size. The first stage aerosol particles then are subjected to heat so as to vaporize the other ingredient of that aerosol and cause further dispersion of that first stage aerosol. As such, a second stage aerosol composed of fine particles of active ingredient is provided. The heat used to cause the further dispersion of the first stage aerosol is less than that sufficient to cause vaporization, thermal decomposition or undesirable chemical alteration of the active ingredient.

13 Claims, 1 Drawing Sheet

AEROSOL DELIVERY ARTICLE

BACKGROUND OF THE INVENTION

The present invention relates to aerosol delivery articles, and in particular, to such articles which are capable of providing aerosol particles of relatively small size while subjecting the material to be aerosolized to relatively low temperatures.

It has been desirable to deliver certain medications to a patient in vapor or aerosol form. As such, the patient inhales the medication, and that medication directly enters that patient's respiratory system. See, *Science*, Vol. 260, p. 912 (1993). As a result, there have been efforts towards developing various aerosol delivery devices, principally for the delivery of certain pharmaceutical compositions or drugs. As used herein, the term "drug" includes articles and substances intended for use in the diagnosis, cure, mitigation, treatment or prevention of disease; and other substances and articles referred to in 21 U.S.C. §321(g)(1). Certain aerosol delivery articles and articles for delivering medicaments in vapor form are described in U.S. Pat. No. 1,771,366 to Wyss et al.; U.S. Pat. No. 1,968,509 to Tiffany; U.S. Pat. No. 2,030,075 to Robinson; U.S. Pat. No. 2,057,353 to Whittemore, Jr.; U.S. Pat. No. 3,820,540 to Hirtz et al.; U.S. Pat. No. 4,036,224 to Choporis et al.; U.S. Pat. No. 4,214,146 to Schimanski; U.S. Pat. No. 4,303,083 to Burruss, Jr.; U.S. Pat. No. 4,735,217 to Gerth et al.; U.S. Pat. No. 4,922,901 to Brooks et al.; and U.S. Pat. No. 4,941,483 to Ridings et al.; as well as by Hickey in *Drugs Pharm. Sci.*, Vol. 54, p.255 (1992). Certain other delivery articles are described in U.S. Pat. No. 3,297,029 to Brinkman et al.; U.S. Pat. No. 3,859,398 to Havstad; U.S. Pat. No. 3,864,544 to Van Amerongen; U.S. Pat. No. 3,990,441 to Hoyt et al.; U.S. Pat. No. 4,190,046 to Virag and U.S. Pat. No. 4,523,589 to Krauser.

Certain of the aerosol delivery articles provide medication in aerosol form by mechanical action. In particular, the medication is provided in the form of an aerosol using nebulizers and metered dose inhalers. Such aerosol delivery articles are desirable in that the pharmacological composition to be aerosolized is not subjected to exposure to heat and high temperatures. However, mechanically generated aerosols typically comprise significant numbers of particles of relatively large size (i.e., greater than about 5 μm in diameter). Such large size particles do not always provide the pharmaceutical composition in a form which provides for maximum effectiveness in treating the patient. Aerosol delivery articles which employ heat to evaporate aerosol forming materials which later condense into aerosol particles of relatively small size provide aerosols which are readily inhaled. However, the pharmacological properties of certain pharmaceutical compositions which are aerosolized by vaporization often are undesirably altered, because certain pharmaceutical compositions are quite sensitive to the effects of heat and temperature.

It would be desirable to provide an aerosol delivery article which is capable of producing aerosol particles of relatively small size (e.g., submicron size) without the necessity of subjecting the material to be aerosolized to exposure to a significant degree of heat or high temperatures.

SUMMARY OF THE INVENTION

The present invention relates to an aerosol delivery article. The article includes an aerosol generating means which is capable of generating an aerosol from a multi-component aerosol forming material. Typically, the aerosol generating means includes a means for mechanically producing aerosol particles from the multi-component material (e.g., a first stage aerosol in the form of a first stage dispersion of aerosol particles). Typically, the multi-component material includes at least one active ingredient to be aerosolized, and at least one other ingredient which provides a capability for causing those first stage aerosol particles to undergo a second stage dispersion or transformation such that aerosol particles of significantly smaller size result. The aerosol delivery article also includes a means for causing the first stage aerosol particles to undergo a second stage dispersion. Typically, the first stage aerosol particles are subjected to heat or other conditions sufficient to destroy the integrity of a significant number of those particles, and hence cause the formation of second stage aerosol particles of relatively small size. Most preferably, the second stage aerosol particles are formed from the active ingredient. The article also includes a delivery means which provides for delivery of the resulting second stage aerosol to the user. Preferably, the aerosol is inhaled by the user into the mouth and/or nose of that user.

In another aspect, the present invention relates to a method for producing an aerosol. A multi-component material capable of forming an aerosol is provided. As such, there is provided an aerosol forming material capable of undergoing a first stage dispersion to form a first aerosol, which first aerosol is capable of undergoing a second stage dispersion to form a second aerosol. The aerosol forming material includes at least one active ingredient and at least one other ingredient capable causing aerosol particles formed from the aerosol forming material to be further dispersed. The aerosol forming material is subjected to conditions sufficient to provide an aerosol from that material. Such conditions typically involve mechanically producing an aerosol from the aerosol forming material, and most preferably involve producing that aerosol under conditions which do not cause the components of that aerosol to experience significant vaporization. The aerosol in the form of a first stage dispersion then is subjected to conditions sufficient to cause a further dispersion of those aerosol particles. Typically, the first stage dispersion is subjected to heat or other conditions sufficient to destroy the integrity of a significant number of those aerosol particles of the first stage dispersion, and hence cause an aerosol in the form of a second stage dispersion of aerosol particles of relatively small size (i.e., of reduced size relative to the first stage aerosol). In such a regard, much of the aerosol of the second stage dispersion can include vapors, gases, and the like. The aerosol so provided then is allowed to pass through a passageway so as to be delivered to the user. As such, an aerosol is delivered into the respiratory system of the user.

DETAILED DESCRIPTION OF THE PREFERRED EMBODIMENTS

Figure 1:
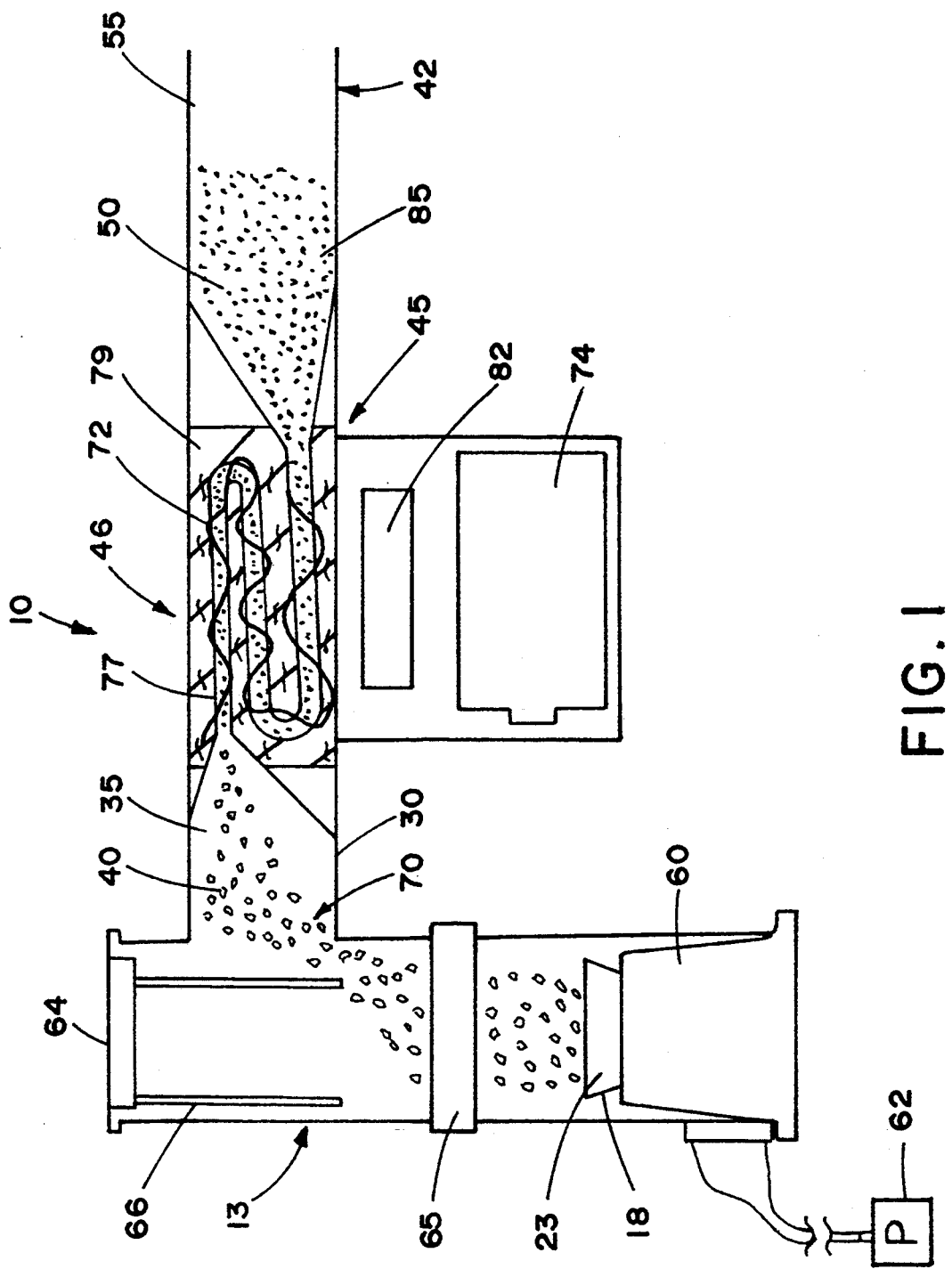
FIG. 1 is a partial sectional view of an aerosol delivery article of the present invention.

Referring to FIG. 1, aerosol delivery article 10 includes an aerosol generator 13 having a reservoir 18 for an aerosol forming material 23; an enclosure member 30 for providing a passageway 35 which allows passage of a first aerosol 40 produced by the aerosol generator through the aerosol delivery article towards mouthend 42 of that article; a heating unit 45, or other suitable means for providing a heating region 46 thus causing the aerosol particles to undergo further dispersion or a transformation to yield a second aerosol 50; and a delivery portion 55, or other suitable means for providing delivery of the second aerosol orally and/or nasally to the user.

The aerosol generator 13 produces a first aerosol 40 from the aerosol forming material 23 contained in the reservoir 18 of that aerosol generator. Typically, the first aerosol 40 is mechanically produced using a nebulizer, or other suitable means for producing an aerosol. A representative nebulizer is available as Microstat Ultrasonic from Mountain Medical Equipment, Inc., Littleton, Colo. Such a nebulizer 13 includes an electrically powered ultrasonic nebulizer head 60 powered by an electrical power source 62; a valve 64 for inlet of drawn atmospheric air; an inner valve 66 for allowing drawn air to pass near the reservoir 18 containing the aerosol forming material 23. A connection collar 65 allows the nebulizer to be assembled and disassembled in order to load that nebulizer with aerosol forming material. The inner valve 66 can be adapted to provide for passage of drawn air containing nebulized aerosol forming material (i.e., the first aerosol 40) out of the aerosol generator through exit passage 70. As such, the inner valve can include a cyclone region (not shown) so as to provide for a fairly lengthy aerosol passage, and a collection cone (not shown) so as to provide for deposition of overly large size aerosol particles back into the reservoir.

The first aerosol 40 exits the aerosol generator 13 and enters a passageway 35. As a practical matter, the passageway also can be provided by a region of the aerosol generator. The passageway can vary in terms of its length, cross-sectional dimensions, construction and format. The length of the passageway typically is quite short in order to keep the dimensions of the article small for ease of use and for ease of draw, and in order to avoid loss of aerosol by deposition so that the concentration of the drawn aerosol is not adversely affected. However, the length of the passageway typically is sufficiently long in order that the first aerosol is given sufficient ability to form without being adversely affected by other components of the aerosol delivery article. For example, for the type of aerosol delivery article shown in FIG. 1, the first aerosol can pass through a passageway of about 5 cm to about 10 cm from the reservoir 18 to the heating unit 45. As such, it is possible to construct the enclosure member 30 from a material (e.g., a heat resistant plastic material such as a polycarbonate or a polyimide) which is adapted so as to have a smooth inner surface in order to provide for ready transfer of aerosol through the passageway. In addition, it can be desirable to construct the enclosure member 30 from a material which has a low coefficient for thermal conductivity, in order that heat generated by the heating unit 45 does not adversely affect the aerosol generator 13 and the formation of the first aerosol 40. The enclosure member 30 can have a variety of shapes, such as a generally tubular shape which is shown in FIG. 1. However, the cross-sectional shape of the enclosure member does not need to be consistent along its length, and can be fruscoconical or helical in shape. Although the cross-sectional area of the passageway can vary, such area typically ranges from about 7 $cm^2$ to about 10 $mm^2$.

The enclosure member 30 then includes a heating unit 45, or other suitable means for causing the first aerosol particles to undergo a further dispersion to yield a second aerosol 50. The heating unit typically includes a region within the enclosure number 30, and such a region can be characterized as a heating region 46. That heating region can have the form of tubes, baffles, or the like. The heating unit provides for a heating region 46 where the first aerosol is heated sufficiently to form the second aerosol, and as such, heat is exchanged between the heating unit and the first aerosol. Exemplary heat exchange units and technology are described in *Perry's Chemical Engineer's Handbook*, Section 11, Sixth Edit. (1984). A case 71 or other means for housing other components of the heating unit 45, typically is provided outside of the enclosure member 30. The case 71 provides a convenient and aesthetic holder or chamber for components of the heating unit which are suited to be positioned outside of the enclosure member 30. Typically, the heating unit generates heat as a result of an electrical resistance heating element 72 and an electrical power source 74. The power source can be a battery power supply having one or more batteries (as shown in FIG. 1) or provided by normal household current stepped down by an appropriate transformer. The resistance heating element 72 and vary in terms of size, composition and configuration. For example, the resistance heating element can be provided by graphite yarns, graphite fabrics, Nichrome film or wire, metal screens, metal or ceramic resistance heating materials, or the like. The resistance heating element also can be in thermal contact with a conducting agent 77 (e.g., an aluminum metal sheet) which is configured so as to distribute heat over a desired region of the aerosol delivery article. As shown in FIG. 1, the resistance heating element 72 is provided by winding a resistance heating wire 72 around a coiled length of metal tubing 77 which acts as a conducting agent for electrically generated heat. It is desirable that the surface temperature of that portion of the heating unit be sufficiently high, the residence time of the aerosol be sufficiently long, and the surface configuration be such to provide a sufficiently high surface area, in order that the aerosol can be adequately heated. The heating region can have the form of a tubular passageway, a coiled passageway, an annular tube, a baffled passageway, passageways having resistance heating screens positioned thereacross, or the like. Typically, the effective length of the passageway of the heating region (i.e., the average distance travelled by the aerosol during heating) is less than about 30 cm, often less than about 25 cm and occasionally less than about 20 cm; but most often is at least about 10 cm. Insulating material 79 (e.g., glass fiber or ceramic fiber) can be positioned within enclosure member 30 so as to surround the tubular conducting agent 77, and hence ensure that heat generated by resistance heating is efficiently used to heat the aerosol.

The manner in which the heat is provided by the heating unit can vary. Typically, the heating unit includes a current regulating means 82 to control the temperature of the heating element, and representative current regulating means are described in U.S. Pat. No. 4,922,901 to Brooks et al., which is incorporated herein by reference. The current regulating means can be time-based in that a particular current can be passed through a particular resistance heating element for a controlled period of time in order that a predetermined temperature can be reached and maintained by a time-based on/off switching mechanism which provides sufficient current over controlled intervals of time to maintain a controlled, essentially constant temperature. Current regulating means which modulate current flow through the heating element can be employed in place of on/off time-based circuits. In addition, on/off and current modulating means can be connected to temperature sensors or other sensing means, rather than to a time-based circuit, in order to control the passage of current through the resistance heating element. Such sensors can be temperature sensors such as infrared sensors, piezoelectric films or the like, or thermostats such as bimetallic strips. Such temperature sensors can sense either the temperature of the resistance element directly or the temperature of the aerosol passing the heating element. Alternatively, the temperature sensors can sense the temperature of a second "model" resistance heating element having a heating and cooling character related to that of the resistance heating element. Another type of sensor which can be employed is a dynamic resistance sensor which senses the change in electrical resistance of the heating element during the heating period.

The heating unit can include a switch (not shown) for turning that heating unit on prior to use, and for turning that heating unit off after use. However, the heating unit can be activated an deactivated by a pressure activated switch (not shown); which is actuated to allow current flow and hence heat generation upon draw, and is deactuated to prevent current flow and hence heat generation when draw ceases. A representative pressure actuated switching mechanism and method for operation in a draw controlled aerosol delivery article are set forth in U.S. Pat. No. 4,922,901 to Brooks et al.

The resistance heating element 72, the electrical power source 74, the current regulating means 82, the switching mechanism, and other electronic components of the heating unit 45 are connected together using known techniques by electrically conductive wires (not shown). As such, one skilled in the art of electronics can provide the circuitry capable of producing heat necessary to cause further dispersion of the first stage aerosol particles 40.

The heat provided by the heating unit acts to alter the character of the first aerosol 40 passing through that region of the aerosol delivery article so as to further disperse that aerosol and form second aerosol 50. The second aerosol passes through a delivery portion 55 which can be equipped to include a cooling region 85. The construction and dimensions of the cooling region can vary depending upon factors such as the temperature of the second aerosol upon exiting the heating region, and the desired temperature of that aerosol immediately upon delivery to the user. The cooling region also can allow for condensation of vaporized aerosol forming material into aerosol particles. Typically, the length of the cooling region ranges from about 1 cm to about 5 cm. For example, the cooling region can be constructed so as to provide for sufficient cooling of heated aerosol and thus provide that aerosol at a palatable temperature (i.e., at about 20° C. to about 40° C.).

In use, the user places aerosol forming material 23 into the reservoir 18 of the nebulizer 13, and provides electrical current (i.e., by using an on/off switch) to power the ultrasonic nebulizer head 60. Alternatively, for other types of aerosol generators, the aerosol forming material is correspondingly placed into the aerosol generator, and prepared for aerosol generation and delivery. For aerosol forming materials in the form of emulsions which can be characterized as stable, the emulsions can be used as such. However, emulsions which can be characterized as unstable may require agitation prior to use. Meanwhile, the heating unit 45 is turned on so as to generate heat in the heating region of the aerosol delivery article. When the heating unit is capable of generating a sufficient amount of heat, the aerosol delivery article is drawn upon at the extreme mouth end 42. However, the heating unit also can be draw controlled in order that current is provided to the resistance heating element immediately upon draw and during the draw period. As such, drawn air entering the aerosol generator through valve 64 is used to provide the first aerosol 40 from the aerosol forming material 18. The first aerosol 40 passes from the aerosol generator 13 through the passageway 35 and is heated in the heating region 46 to provide the second aerosol 50. The second aerosol then passes into the mouth of the user. As such, the finely dispersed particles of the second aerosol 50 can be drawn into, and hence delivered to, the respiratory system (e.g., the nose and/or mouth, throat, and lungs) of the user. As such, fine particles of the active ingredient can be delivered to the respiratory system of the user.

The aerosol forming material is a multi-component material, and as such, includes at least one active ingredient and at least one other ingredient. The active ingredient can include at least one flavoring agent. The flavoring agent can provide fruit, coffee, tobacco, spice flavor or any other desired flavor, to the aerosol. The flavor can be an artificial flavor or natural flavor (e.g., as provided by fruit or tobacco extracts). Ingredients such as glycerine, triethylene glycol and propylene glycol can be ingredients within the multi-component material. The active ingredient most preferably includes at least one pharmaceutical material.

Pharmaceutical materials useful herein most preferably are those which can be administered in an aerosol form directly into the respiratory system of the user. Typical of such materials are drugs or other types of medicaments which are used in the treatment of asthma, pneumonia, influenza, emphysema, bronchitis, epilepsy, depression, shock, respiratory stress in adults and premature infants, hypertension, Alzheimer's disease, Parkinson's disease, cardiac arrhythmia, sinus congestion, allergies, convulsions, anxiety, schizophrenia, hyperactivity, and the like. Examples of suitable drugs include ephedrine; nicotinic compounds such as nicotine, substituted nicotine compounds and metanicotine; metaproterenol; ritaline; resperine; terbutaline; dopamine; phenytoin; lipid molecules; propranolol; diazepam; diphenhydramine; steroids, including cortico steroids such as cortisone, prednisone, triamcinolone and prednisolone; peptide and polypeptide drugs such as are described in *Science*, Vol. 260, p.912 (1993); synthetic pulmonary surfactants such as dipalmitoyl lecithin; and the like. Representative pharmaceutical materials are set forth in U.S. Pat. No. 5,145,861 to Ducep et al.; U.S. Pat. No. 5,109,010 to Beight et al.; U.S. Pat. No. 5,026,861 to Beight et al.; U.S. Pat. No. 4,999,431 to Cheng et al.; U.S. Pat. No. 4,990,519 to Cheng et al.; U.S. Pat. No. 4,886,811 to Cheng et al.; U.S. Pat. No. 4,861,756 to Jackson; U.S. Pat. No. 4,748,274 to Creege et al.; U.S. Pat. No. 4,650,872 to Wright; U.S. Pat. No. 4,622,422 to Creege; U.S. Pat. No. 4,435,420 to Doherty et al.; U.S. Pat. No. 4,405,635 to Dage et al.; and U.S. Pat. No. 4,391,818 to Doherty et al.; as well as by Bowman et al., *Textbook of Pharmacology*, Second Edit. (1980). If desired, the active ingredient can be provided and delivered in a buffered or salt form. As such, fine aerosol particles of an active ingredient can be provided in a salt form during delivery, because the first stage aerosol particles can be produced in such a manner (e.g., nebulized from an emulsion) such that the active ingredient can be provided in aerosol form in salt form, and the first stage aerosol can be further dispersed into a plurality of smaller sized aerosol particles in a manner such that the salt nature of the active ingredient is maintained.

The other ingredient of the aerosol forming material can vary. That ingredient can have a solid or liquid form. If desired, that ingredient can include two or more components, and combinations of solid and liquid components can be employed. Most preferably, the other ingredient does not act as a solvent for the active ingredient (e.g., the active ingredient and other ingredient are essentially immiscible with one another). As such, the active ingredient and other ingredient each are localized in various locations throughout the first aerosol particles. The other ingredient most preferably does not chemically interact with the active ingredient and does not significantly alter the pharmacological activity of the active ingredient during normal conditions of storage and use. The other ingredient preferably is of a nature, and is used in an amount, such that the other ingredient is essentially pharmacologically inactive relative to the active ingredient. However, it is possible that both the active ingredient and other ingredient can provide pharmacological effects. The active ingredient is of a nature and character such that aerosol particles can be generated from the multi-component material incorporating that ingredient. That ingredient is such that when aerosol particles incorporating that ingredient are subject to certain conditions (e.g., the application of heat), those aerosol particles are further dispersed into aerosol particles of smaller size.

The aerosol forming material can have the form of microcapsules containing a volatile material dispersed within a continuous phase of active ingredient (e.g., active ingredient in neat form or as a solution within a suitable solvent). As such, when an aerosol provided from such a dispersion is provided and subjected to conditions (e.g., heat) sufficient to volatilize the material within the microcapsules, the microcapsules decompose (e.g., explode) thereby causing the dispersion of the aerosol particles of the active ingredient which was incorporated within such microcapsules. If desired, other ingredients can be incorporated into the microcapsules in order to ensure that the active ingredient is dispersed into a plurality of aerosol particles of small size.

The aerosol forming material can have the form of microsponges containing a volatile material dispersed within a continuous phase of active ingredient (e.g., active ingredient in neat form or as a solution within a suitable solvent). As such, when an aerosol provided from a dispersion of such microsponges is provided and subjected to conditions (e.g., heat) sufficient to volatilize and release the volatile material held within the microsponges, the resulting volatilized material causes the dispersion of the active ingredient which was incorporated within such microsponges. The dispersed active ingredient has the form of a plurality of aerosol particles.

The aerosol forming material can have the form of an emulsion. See, U.S. Pat. No. 4,655,959 to Stopper and U.S. Pat. No. 5,145,604 to Neumiller; and Hiemenz, *Principles of Colloid and Surface Chemistry*, p. 467–474 (1986); and Friberg, et al., *Microemulsions: Structure and Dynamics* (1987). Such an emulsion typically includes a continuous phase of active ingredient (e.g., active ingredient in neat form or as a solution within a suitable solvent) and a dispersed phase of a volatile material. If desired, the emulsion can include surfactants (e.g., cationic, anionic or nonionic surfactants), or other surface active agents capable of providing the desired properties to that emulsion. Emulsions can be provided by contacting immiscible components, other ingredients such as surfactants, and shearing or otherwise mechanically agitating the mixture of components. Typically, the dispersed phase provides about 1 percent to about 50 percent, usually about 5 percent to about 40 percent, and often about 10 to about 30 percent, of the volume of the emulsion. Typically, the active ingredient can be non polar or hydrophobic in character, making a dispersed phase provided by a material having a polar character particularly desirable. Exemplary materials suitable for forming a dispersed phase include water, ethanol, and the like. It also is possible, for certain active ingredients, to disperse or dissolve the active ingredient in a polar liquid (e.g., water) and to employ such a mixture as a continuous phase, and to employ a nonpolar liquid (e.g., a hydrocarbon or a halogenated hydrocarbon) as a dispersed phase component.

The aerosol forming material can be provided as a first stage aerosol by separately providing immiscible ingredients, separately mechanically dispersing the ingredients (e.g., by nebulizing those separated ingredients at the same time), and allowing the components of the dispersed mixture to coagulate within the aerosol delivery article to form multi-component aerosol particles. These first stage aerosol particles later can be subjected to heat so as to further disperse the coagulated components within the individual first stage aerosol particles.

The multi-component aerosol forming material also can contain a reactive component (e.g., a blowing agent which produces carbon dioxide or other gas) when subjected to certain conditions within the aerosol delivery article. The production of gaseous material by components within the aerosol particles have the capability of causing first stage aerosol particles containing such blowing agents to be destroyed, and hence cause dispersion of active ingredient.

The multi-component aerosol forming material is such that it can readily generate an aerosol. As such, the physical form preferably is such that the multi-component material is relatively stable, and can be stored for reasonable periods of time prior to use. The individual components of the aerosol forming material are such that there is not experienced adverse affect upon the active ingredients by the other ingredients during storage.

The aerosol delivery article includes an aerosol generator which provides a first stage aerosol from a multi-component material. The aerosol generator most preferably provides an aerosol from the aerosol forming material at a temperature below the temperature at which at least one active ingredient of the multi-component aerosol forming material is vaporized, thermally decomposed or altered chemically under normal atmospheric conditions. As such, it is most preferable that the aerosol is not formed solely by the action of heat upon the aerosol forming material. Typically, the first stage aerosol is formed at near ambient temperatures. Most preferably, the first stage aerosol is provided mechanically. Typically, the first stage aerosol is provided from a nebulizer, an atomizer, a metered-dose inhaler, a dry powder inhaler, or other suitable aerosol generator. See, Hickey, *Drugs Pharm. Sci.*, Vol. 54, p. 255 (1992). Representative devices for providing aerosols are set forth in U.S. Pat. No. 2,284,591 to Rose; U.S. Pat. No. 2,332,799 to Hunn et al.; U.S. Pat. No. 2,764,154 to Murai; U.S. Pat. No. 4,655,229 to Sensabaugh et al.; U.S. Pat. No. 4,715,387 to Rose and U.S. Pat. No. 4,765,347 to Sensabaugh et al.

The first stage aerosol so provided passes through the aerosol delivery article. As such, the first stage aerosol travels through a passageway from the aerosol generator to a region having means capable of further dispersing the first stage aerosol particles or otherwise causing components of the first stage aerosol to be released from the particles making up that first stage aerosol. As such, it is most preferable that the first stage aerosol comprises particles of multi-component aerosol forming material dispersed within a gas phase. The gas phase most preferably is composed predominantly of atmospheric air; however, the gas phase also can include propellant used to generate the first stage aerosol.

The average size of the individual first stage aerosol particles can vary. Typically, the mass average size of those particles is at least about 5 $\mu$m in diameter, often at least about 10 $\mu$m in diameter, and frequently at least about 15 $\mu$m in diameter. Typically, the mass average size of those particles does not exceed about 50 $\mu$m, often does not exceed about 40 $\mu$m, and frequently does not exceed about 30 $\mu$m.

The first stage aerosol has a character such that the aerosol is stable and does not have a tendency to undergo an undesirable degree of deposition within the aerosol delivery article. The aerosol contains sufficient active ingredient for a dose, and such amount depends upon the selected active ingredient. For most applications, the first aerosol comprises about 0.1 mg to about 40 mg aerosol particles per 200 ml of drawn air.

The first stage aerosol, after it has been formed, then is subjected to conditions sufficient to form second stage aerosol particles of relatively small size as compared the first stage aerosol particles. In one regard, the integrity of a significant number of the first stage aerosol particles is destroyed (e.g., in the case of a multi-component aerosol forming material in the form of an emulsion). In another regard, at least one active ingredient is released from substrates in the form of aerosol particles (e.g., in the case of active ingredient carried by a microsponge particle). The manner in which the second stage aerosol is formed can vary. However, the preferred method for forming the second stage aerosol involves subjecting the first stage aerosol to conditions of heating by increasing the temperature of that first stage aerosol. Most preferably, the first stage aerosol is subjected to conditions of elevated temperature sufficient to alter the physical character of certain components of that first stage aerosol. That is, the first stage multi-phase aerosol particles (e.g., coarse, mechanically generated aerosol articles) are treated in a manner so as to cause those particles to undergo a mechanical disruption so as to be dispersed into second stage aerosol particles of finer size. For example, certain components of the first stage aerosol particles (e.g., components in solid or liquid form) can be vaporized by the application of heat to cause destruction (i.e., break up) of those first stage aerosol particles. As such, there is a significant change in the physical character of the first stage aerosol, as opposed to a simple warming of the first stage aerosol. As a result, a second stage aerosol typically is provided by the action of heat. However, those conditions of elevated temperature or heat to which the first stage aerosol particles are subjected most preferably are not so severe so as to adversely affect the desired activity of the active ingredient. As such, it is preferable to subject the first stage aerosol particles to heat sufficiently great to cause a change in physical character to at least one component of the multi-component first stage aerosol particles, while not subjecting that first stage aerosol to heat sufficiently great to cause an adverse change in the active ingredients of the multi-component first stage aerosol particles. Typically, the heat to which the first stage aerosol particles is subjected is below that required to provide vaporization, thermal decomposition or undesirable chemical alteration of the active ingredients. As a result, small size aerosol particles can be generated without evaporating and condensing the material used to generate those particles.

The amount of heat experienced by the first stage aerosol can vary. The amount of heat which that aerosol experiences depends upon factors such as the temperature within the region that the aerosol is subjected to heat, the amount of time that the aerosol passes through that region, the rate at which the aerosol passes through that region, and the size of that region. The first aerosol typically is subjected to a sufficient amount of heat so as to cause the aerosol particles of that first aerosol to undergo further dispersion. Typically, such further dispersion is provided by heating to a significant degree the air component of the first aerosol. Typically, for a drawn volume of 200 ml, the heat required to heat a first aerosol of the present invention by at least about 100° C. is greater than about 5.5 calories, often is greater than about 6.0 calories and frequently is greater than about 6.5 calories. Typically, at least a portion, and preferably essentially all, of the aerosol is heated to a temperature of at least about 50° C., often at least about 75° C., frequently at least about 100° C., occasionally at least about 120° C., and sometimes at least about 150° C. Typically, a significant amount of the aerosol is not subjected to heating to a temperature above about 400° C., and often is subjected to heating to a temperature below about 300° C., and frequently is subjected to heating to a temperature below about 200° C. As such, it is highly preferred that the aerosol is not subjected to sufficient heat to cause combustion of certain components of that aerosol.

It is desirable to provide efficient heating of the first aerosol without causing significant deposition of the particulate material of which that aerosol is composed. As such, it is desirable to provide convective or radiant heating of the aerosol particles using a high temperature heating unit having a surface area and configuration so that a significant amount of the aerosol particles does not experience contact with components of that heating unit. Alternatively, it is desirable to provide conductive heating to the aerosol particles using a heating unit operated at a moderate temperature, and having a surface area and configuration so that a significant amount of the aerosol particles does experience contact with certain components of that heating unit in order to transfer the desired level of heat to the aerosol particles.

The surface temperature of certain components of the heating region can vary. That surface temperature depends upon factors such as the surface area of that region (e.g., which can depend upon the configuration and length of the region), and the temperature to which the aerosol is desired to be heated. For many applications, it is desirable that the surface temperature of that portion of the heating unit be below about 600° C., often below about 500° C., and frequently below about 400° C. For most applications, it is desirable that the surface temperature of the heating region be at least about 200° C., sometimes at least about 250° C., and occasionally at least about 300° C. However it is most desirable that the surface temperature of the heating region be between about 200° C. and about 300° C. Typically, first aerosols of the present invention can be heated so as to experience an increase in temperature of at least about 100° C. upon passing through a passageway of a heating region having an effective length of about 10 cm to about 30 cm and a surface temperature of about 200° C. to about 300° C. See, *Fundamentals of Heat and Mass Transfer*, Third Edit., Incropera and DeWitt, Chapter 8 (1990).

The average size of the individual second stage aerosol particles can vary. The average size of those individual aerosol particles is significantly less than the average size of the individual aerosol particles of the first stage aerosol. Typically, the mass average size of the aerosol particles of the second stage aerosol is less than about 5 $\mu$m, often is less than about 3 $\mu$m, and frequently is less than about 1 $\mu$m. Typically, the mass average size of the aerosol particles of the second stage aerosol is at least about 0.2 $\mu$m, and often at least about 0.5 $\mu$m. Submicron size aerosol particles are desirable for many applications. Normally, the aerosol particles are provided by the active ingredient of the aerosol forming material. Aerosol particles also can be provided, at least in part, by solvents or other ingredients with the aerosol forming material. Typically, a significant amount of the second stage aerosol can be provided in the form of a vapor provided by vaporization of certain components of the multi-component aerosol forming material. The small size of the particles making up such an aerosol makes that aerosol readily inhalable and allows for effective delivery to the respirator system of the user. There is a large inhalable mass fraction of particulate material. There is also a significant increase in the number of aerosol particles within the second aerosol as compared within the second aerosol as compared to the first aerosol (e.g., often about 10 to about 100 times more). In addition, cooling of vaporized material can result in aerosol particles formation due to condensation on the larger number of second stage aerosol particles. The concentration of particulate and vaporized material within the second aerosol is approximately equal to that of the first aerosol which is subjected to further dispersion, although a small portion (e.g., up to about 10 percent) of the aerosol can be lost (e.g., by deposition or otherwise) during passage through the aerosol generating article.

The second stage aerosol is delivered to the user. The manner in which that aerosol is delivered can vary, and that aerosol can be delivered into the mouth and/or nose of the user. The manner of delivery can depend upon factors such as the identity of the active ingredient and the manner of treatment desired. As such, the delivery portion can vary in terms of size, construction and configuration. Typically, the delivery portion includes a passageway to allow the aerosol to pass to the user, and a configuration which allows the user to receive the aerosol. Exemplary delivery portions for delivering aerosol into the mouth of the user (i.e., mouthend pieces) have generally tubular constructions, and have a size so that the delivery portion can readily fit into the mouth of the user. Exemplary delivery portions for delivering aerosol through the nose of the user (i.e., a nasal covering) have a construction and size so as to fit over the nasal cavity of the user. Exemplary delivery portions for delivering aerosol into the nose and mouth of the user are configured so as to fit over the relevant area of the face of the user. As such, the user can receive aerosol into his/her respiratory system by drawing on (i.e., inhaling through) the mouthend of the article and/or by inhaling through the nasal covering of the article. Selection of the particular design of the delivery portion will be apparent to the skilled artisan.

What is claimed is:

1. An aerosol delivery article incorporating a multi-component aerosol forming material, the article comprising:
   a) an aerosol generating means for mechanically producing a first aerosol including a dispersion of first aerosol particles from a multi-component aerosol forming material, the first aerosol including a first dispersion of first aerosol particles of the aerosol forming material in a gas phase;
   b) means for causing the first aerosol particles to be dispersed into second aerosol particles having an average size smaller than that of the first aerosol particles., said first aerosol particles being dispersed into second aerosol particles by heating means for applying heat to the first aerosol so as to destroy the physical integrity of the first aerosol particles and to provide a second aerosol including a second dispersion of particles of at least one component of the aerosol forming material in a gas phase; and
   c) means for delivering the second aerosol particles, in aerosol form, to a user.

2. An aerosol delivery article comprising:
   a) an aerosol generating means for producing a first aerosol from a multi-component aerosol forming material, the first aerosol including a first dispersion of particles of the aerosol forming material in a gas phase;
   b) means for heating the first aerosol so as to destroy the physical integrity of the particles of the first dispersion so as to provide a second aerosol including a second dispersion of particles having an average size smaller than that of the first dispersion of particles, and said second dispersion of particles of at least one component of the aerosol forming material in a gas phase;
   c) means for delivering the second aerosol to a user.

3. The article of claim 1 wherein the multi-component aerosol forming material has the form of an emulsion having (i) a dispersed phase including at least one active ingredient, and (ii) a continuous phase including at least one other ingredient.

4. The article of claim 3 wherein the active ingredient is essentially water insoluble and the other ingredient is water.

5. The article of claim 4 wherein the aerosol generating means is capable of producing the first aerosol at a temperature below about 50° C., and the means for causing the first aerosol particles to be dispersed into second aerosol particles is capable of heating the first aerosol so as to vaporize the water component thereof.

6. The article of claim 1 wherein the means for delivering the second aerosol to the user is a mouth end piece.

7. A method for delivering an aerosol provided from a multi-component aerosol forming material into a user's respiratory system, the method comprising:
   a) providing a multi-component aerosol forming material;
   b) mechanically producing a first aerosol from the aerosol forming material thereby dispersing particles of the aerosol forming material within air;
   c) subjecting the first aerosol to conditions sufficient to cause further dispersion of the aerosol particles of the first aerosol, thereby providing a second aerosol, said aerosol particles of the first aerosol being dispersed into second aerosol particles by applying heat to the first aerosol so as to destroy the physical integrity of the aerosol particles of the first aerosol and to provide a second aerosol including a second dispersion of particles having an average size smaller than that of the first dispersion of particles, and said second dispersion of particles of at least one component of the aerosol forming material in a gas phase; and
   d) providing passage of the second aerosol to the user.

8. The method of claim 7 whereby the first aerosol so provided has a mass average particle size of at least about 5 μm in diameter.

9. The method of claim 7 whereby the first aerosol so provided has a mass average particle size of at least about 10 μm in diameter.

10. The method of claim 8 whereby the first aerosol so provided has a mass average particle size which does not exceed about 50 μm.

11. The method of claim 8 whereby the first aerosol is produced at a temperature below about 50° C., and the first aerosol so formed is subjected to conditions sufficient to disperse the first aerosol particles to particles of reduced size.

12. The method of claim 11 whereby the first aerosol, after being formed, is subjected to a temperature of at least about 100° C. but not above about 400° C.

13. The method of claim 7 whereby the second aerosol so provided has a mass average particle size of less than about 1 μm.

* * * * *